United States Patent
Guo et al.

(10) Patent No.: US 7,247,656 B2
(45) Date of Patent: Jul. 24, 2007

(54) MEMBRANE-ENHANCED LIQUID PRODUCTION FOR SYNGAS HUBS

(75) Inventors: Chang-Jie Guo, Exton, PA (US); Paul Wentink, Feucherolles (FR)

(73) Assignee: L'Air Liquide, Société Anonyme à Directoire et Conseil de Surveillance pour l'Étude et l'Exploitation des Procedes Georges Claude, Paris (FR)

( * ) Notice: Subject to any disclaimer, the term of this patent is extended or adjusted under 35 U.S.C. 154(b) by 1 day.

(21) Appl. No.: 11/066,866

(22) Filed: Feb. 25, 2005

(65) Prior Publication Data

US 2006/0194889 A1    Aug. 31, 2006

(51) Int. Cl.
C07C 27/00    (2006.01)
(52) U.S. Cl. .................. 518/706; 518/700; 518/702; 518/703; 518/705; 518/726
(58) Field of Classification Search ........ 518/700–706, 518/707, 726
See application file for complete search history.

(56) References Cited

U.S. PATENT DOCUMENTS

| | | | |
|---|---|---|---|
| 6,495,610 B1 | 12/2002 | Brown | |
| 6,596,781 B1 | 7/2003 | Schinski | |
| 2002/0006968 A1 | 1/2002 | Abbott | |
| 2003/0223931 A1 | 12/2003 | Narayan | |
| 2004/0102532 A1* | 5/2004 | Landis et al. | ............... 518/726 |

OTHER PUBLICATIONS

PCT International Search Report dated May 9, 2006.

* cited by examiner

Primary Examiner—J. Parsa
(74) Attorney, Agent, or Firm—Christopher J. Cronin (57) ABSTRACT

This disclosure discusses problems associated with using natural gas to produce a variety of synthetic hydrocarbon products by production processes that require syngas feedstocks with varying H2/CO and (H2–CO2)/(CO+CO2) ratios. A number of gas separation membranes are used to vary the composition of the feed streams to different hydrocarbon synthesis units so that different synthetic hydrocarbon products can be produced. The process supplies syngas to an integrated hydrocarbon processing system comprising a number of hydrocarbon synthesis units. Gas (usually a portion of a raw syngas stream) is routed through the separation membrane units, multiple H2-rich and H2-lean streams are produced. These H2-rich and H2-lean streams can then be combined in a controlled fashion to produce feed streams of the desired compositions for the various hydrocarbon synthesis units. A variety of liquid synthetic hydrocarbon products can be produced from a given syngas source as required by market demands.

10 Claims, 3 Drawing Sheets

MEMBRANE-ENHANCED LIQUID PRODUCTION FOR SYNGAS HUBS

BACKGROUND

This invention relates to the conversion of natural gas to syngas, and then to liquid hydrocarbons that are easily transported.

Substantial proportions of known natural gas reserves are situated in locations remote from areas of high consumption. There is about 3.5 TCF (100 billion cubic meters) of natural gas flared annually worldwide. Nearly 40% is in Africa, and ~17%, ~12%, and ~17% in North America, Central and South America, and the Far East & Oceania respectively. The amount of natural gas being flared is estimated to be equivalent to 900,000 barrels per day (bpd) of liquid product. Conversion of both stranded gas and associated gas into a transportable and saleable form of products is a major challenge and at the same time represents enormous business potential.

Natural gas can be liquefied and transported to larger users. For example, Liquefied Natural Gas (LNG) accounts for 97% of Japan's natural gas supply. LNG accounts for about 90% of the outlet for stranded gas, with methanol at 7% and Fischer-Tropsch/Gas to Liquid (F-T/GTL) less than 2%. LNG, however, is capital-intensive and is typically only economically viable for large gas reserves located at coastal sites. The large investment required and the small number of receiving terminals limit the marketing flexibility of LNG.

An alternative to LNG is the gas to liquid (GTL) route that converts natural gas into synthetic fuels ranging from gasoline to middle distillates, as well as to methanol and other liquids. This approach avoids the infrastructure limitations associated with LNG and at the same time provides a market that is large enough to accept the potentially large volumes of product. Synthetic liquids and other synthetic petroleum products are clean and cheaper to transport, market, and distribute to large markets than LNG. They can be transported in existing pipelines or product tankers and even blended with existing crude oil pools. Furthermore, no special contractual arrangements are required for their sale, and such fuels are not subjected to OPEC regulations. GTL products offer an advantage to conventional fuels in that the low sulfur content of the GTL fuels leads to significant reductions in particulate matter that is generated during combustion. Their low aromatic content reduces the toxicity of the particulate matter. There is a worldwide trend towards the reduction of sulfur and aromatics in fuel. These factors are major drivers behind the GTL process development and investment.

U.S. Pat. Nos. 6,596,781 and 6,495,610 describe processes that produce syngas that is used in more than one type of GTL process. However, these processes suffer from one or more of the problems described below.

The scale-up exponent (cost is a constant times capacity $^y$) of GTL plants is estimated to be 0.66. In the absence of a breakthrough technology, therefore, economies of scale are the only significant mechanism by which GTL can achieve economic viability. At present large fields will have LNG and F-T processes followed by other natural gas consumers whereas smaller fields will accommodate large methanol units producing 10,000 tons per day (TPD) methanol which will flood the methanol market.

To prevent flooding the market with a single GTL product, it is desirable to be able to convert a large amount of natural gas into syngas, and then distribute the syngas to a variety of GTL processes. Depending on market demand and other factors, different types of products can be produced at different rates from a large-scale syngas generation hub. Some of the products that may typically be produced are middle distillate/diesel, gasoline, methanol (MeOH), dimethyl ether (DME), lubricants, or other liquid hydrocarbons. Using a large-scale syngas hub also allows the use of moderate size DME units without the normal investment penalty for smaller scale plants. However, distributing the syngas to various processes suffers from the following problems:

1) The requirement for syngas composition (e.g., H2/CO) by different liquid products is quite different. Thus, the same syngas composition cannot be fed to a variety of GTL processes.
2) The range of syngas composition that can be produced by a single synthesis unit (such as an autothermal reforming plant (ATR)) is limited by factors such as steam/carbon ratio, etc.

Thus, ATR units are typically designed to produce a relatively narrow range H2/CO ratio syngas. For example, if the ATR is producing syngas to be fed to an F-T unit, the unit will be designed to produce a syngas with a H2/CO ratio of about 1.9.

To address the limitations imposed by syngas unit designs, it is desirable to develop a process wherein the H2/CO ratio of the syngas can be adjusted after leaving the syngas production unit without wasting a significant amount of the gas produced. Specifically, it is desirable to adjust the H2/CO and (H2−CO2)/(CO+CO2) ratio, to meet specifications required by different liquid production processes that are integrated with the syngas production unit to convert the syngas into easily transportable liquid hydrocarbon products.

SUMMARY

The present invention is directed to a process that satisfies the need to provide a process wherein syngas can be produced in a single large syngas production site while still supplying feedstock to multiple gas to liquid (GTL) processes that require substantially different syngas compositions without wasting a significant amount of the syngas produced. The current invention provides a process for converting syngas into multiple products, wherein the process takes a raw syngas comprising $H_2$ from a syngas-generating unit and supplies the syngas to an integrated hydrocarbon processing system. The integrated hydrocarbon processing system contains a number of various hydrocarbon synthesis units and a number of H2 selective separation membrane separator units. By routing gas through the separation membrane units, multiple H2-rich and H2-lean streams are produced. These H2-rich and H2-lean streams can then be combined in a controlled fashion to produce feedstreams for the various hydrocarbon synthesis units of the desired compositions (desired H2/CO and (H2−CO2)/ (CO+CO2 ratios)). Finally, various liquid synthetic hydrocarbon products can be produced as required by market demands by feeding the various composition streams to the appropriate hydrocarbon synthesis unit.

Depending on market demand and other factors, different types of products, such as middle distillate/diesel, gasoline, methanol (MeOH), dimethyl ether (DME), lubricants, and other hydrocarbon liquids, are produced at different rates from a large syngas generation hub. Hydrogen selective membranes can be utilized and integrated into the overall syngas conversion schemes to effectively adjust the composition of the syngas, specifically the H2/CO and (H2−CO2)/

(CO+CO2) ratio, to meet various specifications required by different liquid production processes. The integration of membranes enhances significantly the flexibility of a production site and minimizes the loss of valuable gases such as H2 and CO. The syngas can then be converted into various transportable liquid hydrocarbon products to meet market requirements.

For instance, a syngas stream with a H2/CO of 1.9 (for a F-T liquid), a syngas stream with a H2/CO ratio of about 1.0 (for DME), and a syngas stream with a (H2−CO2)/(CO+CO2) ratio of 2.05 (for methanol) are produced by partially treating the raw syngas stream of a H2/CO ratio 2.1 to 2.3. The net generation of high purity H2 (by combining membrane and PSA) can be adjusted as well depending on specific supply-demand scenarios of a specific hub.

The advantage of a syngas hub is to achieve economy of scale for a large part of the investment for different products. An air separation unit (ASU) and a syngas section for both methanol and F-T, is between 50-65% of the investment. This approach will increase the viability of projects under consideration by companies who have not fully developed their resources using F-T technology, as it allows exploitation of smaller gas fields. With product diversification on smaller gas fields the likelihood of advancing projects increases.

In one preferred embodiment, the integrated hydrocarbon processing system comprises a first synthesis unit, a second synthesis unit, a first membrane separator, and a second membrane separator. The process feeds a first portion of the raw syngas to the first membrane separator where a first H2-lean syngas and a first H2-rich syngas are separated from the first portion of the raw syngas. Next, a first H2-adjusted syngas is formed by combining a second portion of the raw syngas with the first H2-lean syngas, a second H2-lean syngas, or a combination thereof. The first H2-adjusted syngas is formed by controlling the relative amounts of the second portion of the raw syngas and the first H2-lean syngas combined to result in a composition ratio in the first adjusted syngas that is proper for the optimum production of synthetic hydrocarbon products in the first synthesis unit. The process also feeds a third portion of the raw syngas to the second membrane separator where the second H2-lean syngas and a second H2-rich syngas are separated from the third portion of the raw syngas. A second H2-adjusted syngas is formed from the first H2-lean syngas, the second H2-lean syngas or a combination thereof, which is fed to the second synthesis unit to produce a second synthetic hydrocarbon product.

In alternate embodiments:
the first synthesis unit is an F-T synthesis unit;
the second synthesis unit is a DME synthesis unit;
the integrated hydrocarbon processing system further comprises a third synthesis unit, and the process forms a third H2-adjusted syngas by combining a fourth portion of the raw syngas and the first H2-rich syngas, the second H2-rich syngas, or some combination thereof. The third H2-adjusted syngas is formed by controlling the relative feed rate of the streams to form a single stream with an effective composition (such as (H2−CO2)/(CO+CO2) ratio) for the production of a third synthetic hydrocarbon product;
the third synthesis unit is a MeOH synthesis unit;
the raw syngas has an H2/CO ratio of above about 1.8;
the first H2-adjusted syngas has an H2/CO ratio of less than about 2.1;
the second H2-adjusted syngas has an H2/CO ratio of below about 1.8;
the third H2-adjusted syngas has a (H2−CO2)/(CO+CO2) ratio of above about 1.8;
the first membrane separator comprises a membrane comprising polyimide polymers;
the second membrane separator comprises a membrane comprising ceramic materials;
the integrated hydrocarbon processing system includes a PSA unit, and the first H2-rich syngas is fed to the PSA unit to form a substantially pure H2 stream from the PSA unit; and
the integrated hydrocarbon processing system includes an ATR unit wherein a natural gas feed reacts with an oxygen stream to form the raw syngas.

The current invention is not limited to the alternatives summarized above. Other combinations of integrated hydrocarbon processing units and separation membranes, some of which are described in the description section below, may also be created to form the proper products in the proper amounts. The current invention provides for the integration of a large syngas production unit, or hub, wherein syngas is produced at a given H2/CO ratio, which can be varied after syngas production using various combinations of raw syngas feed and membrane separators. The raw syngas and separated streams are controllably combined to form feeds streams for the hydrocarbon synthesis units of the desired composition to efficiently produce the desired synthetic hydrocarbon products.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

The process of the present invention integrates a large syngas production hub with a variety of synthetic hydrocarbon processes using hydrogen-selective separation membranes to adjust the composition of the syngas to meet the requirements of the various processes. Thus, a variety of synthetic hydrocarbon products may be produced from a single syngas source of a given single composition.

The term hydrocarbon synthesis unit, as used in this application, can be various processes known in the art for conversion of syngas into synthetic hydrocarbon products. The hydrocarbon synthesis units may comprise synthesis reactors, liquid/vapor separation systems, product upgrading units, such as hydrocracking, and/or other processes. Hydrocarbon synthesis processes may include Fischer-Tropsch (F-T) processes, or other gas to liquid processes (GTL), known to one skilled in the art.

As used herein, the term "syngas" describes the gas comprising primarily carbon monoxide (CO) and hydrogen (H2) that is produced by a synthetic process. Syngas is produced from hydrocarbon feedstocks by any of a number of processes known to those skilled in the art, such as steam methane reforming (SMR), autothermal reforming (ATR)

and gasification (or partial oxidation). One preferred syngas process converts natural gas feedstocks with the use of oxygen.

As used herein, the term "raw syngas" describes the syngas produced from the synthetic production process before the H2/CO ratio is adjusted.

As used herein, the term "hydrocarbon synthesis unit" describes various processes known to one skilled in the art for converting syngas into synthetic petroleum products. Typical processes are, but are not limited to, Fischer-Tropsch (F-T) or chain growth reaction of carbon monoxide and hydrogen on the surface of a heterogeneous catalyst. Hydrocarbon synthesis units may comprise various sub-parts, such as a gas to liquid reaction zone, liquid/vapor separation zone, product hydrocracking units, and product fractionators.

As used herein, the term "PSA unit" describes a plant or unit that separates gases from a feed stream by a principle known as pressure swing adsorption. One skilled in the art is familiar with the use of PSA units for separating hydrogen from a hydrogen-containing stream to create a substantially pure H2 stream. The substantially pure H2 stream is greater than about 95 mole percent hydrogen, preferably greater than about 99 mole percent hydrogen, and even more preferably about 99.9 mole percent hydrogen. The PSA unit also produces a combustible tail gas that comprises primarily CO, carbon dioxide (CO2), and methane that can be burned in a utility generation unit.

As used herein, the term "membrane separator" describes a device which provides the separation of H2 from a gaseous feedstream. The hydrogen is separated by preferential permeation of H2 over CO or CO2 or other ordinary gases encountered in a syngas plant. Any type of membrane materials favorable to the separation of H2 and CO/CO2, known to one skilled in the art, are acceptable. Any type of construction for membrane separators may be used, although hollow-fiber type is preferred for its compactness and high separation efficiency.

Figure 1:
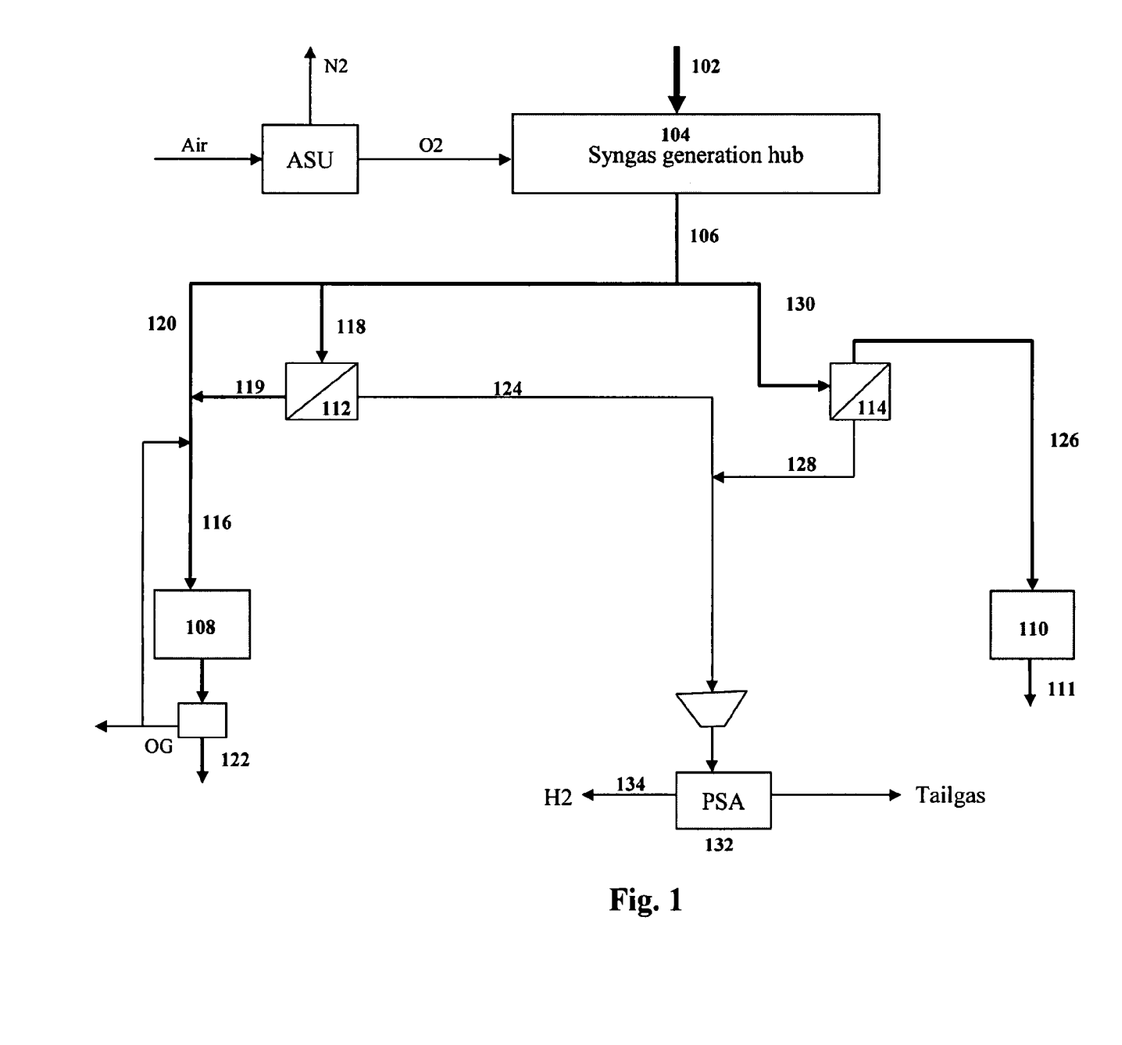
FIG. 1 is a schematic diagram of one embodiment of the current invention.

Referring to FIG. 1, a feedstock 102 is fed to a large syngas production hub 104 where it is converted into raw syngas 106 containing hydrogen. The raw syngas 106 can then be converted into multiple products in an integrated hydrocarbon processing system comprising at least two membrane separators 112, 114 and at least two synthetic hydrocarbon synthesis units 108, 110 by adjusting the composition of the raw syngas 106 in at least two membrane separators 112, 114. The feedstock 102 can be any carbonaceous feedstock. For example, one preferred feedstock is natural gas. The syngas production hub 104 is any of a variety of processes known to one skilled in the art for converting a carbonaceous feedstock into a synthetic gas. One preferred process converts natural gas to syngas by an autothermal reforming (ATR) process. The raw syngas of the current invention comprises predominantly hydrogen (H2) and carbon monoxide (CO), but also contains carbon dioxide (CO2), hydrocarbons, and other materials. A preferred raw syngas contains about 40 to about 80 mole percent H2. Another preferred raw syngas contains about 50 to about 70 mole percent H2. Furthermore, the H2/CO ratio of the preferred raw syngas is greater than about 1.8, even more preferred is greater than about 2.0. Still further, one preferred embodiment uses a raw syngas with an H2/CO ratio of about 2.1, whereas another preferred embodiment uses a raw syngas with an H2/CO ratio of about 2.3. These ranges are not absolute and are subject to change with changing feedstocks.

Still referring to FIG. 1, the hydrocarbon synthesis units are any of a variety of processes known to own of ordinary skill in the art for converting syngas into usable synthetic hydrocarbon products. The preferred processes are gas to liquid (GTL) processes that convert syngas into liquid hydrocarbon products that can easily be shipped without the need for a cryogenic liquefaction step. Preferred processes include F-T, MeOH, and DME production processes.

In the embodiment shown in FIG. 1, at least one membrane separator 112, preferably multiple membrane separators 112, 114, is used to adjust the H2/CO ratio of the raw syngas 106 before being fed to a number of hydrocarbon synthesis units 108, 110. The membrane separators 112, 114 contain any membranes known to one of ordinary skill in the art that have effective selectivity for H2 over CO, or CO2 over CO. One preferred membrane comprises polymeric materials that comprises polyimide or polyaramide polymers. Another preferred membrane is based on ceramic materials (usually when syngas temperature is higher than 300° C.). Another preferred membrane is a blend of a polyimide with a polyamide and/or polyamide-imide polymers. A preferred membrane would be a hydrogen or carbon dioxide selective membrane, wherein hydrogen or carbon dioxide is the predominant permeate fluid. The process forms at least one H2-adjusted syngas stream 116 of different compositions (i.e H2/CO or (H2−CO2)/(CO+CO2) ratio) effective for the production of a desired synthetic hydrocarbon product. The H2-adjusted syngas stream 116 may have an H2/CO ratio that is either higher or lower than the raw syngas 106. In one preferred embodiment exemplified in FIG. 1, at least one H2-adjusted syngas 116 is produced by feeding a first portion of raw syngas 118 to a membrane separator 112 to produce an H2-lean syngas 119. The H2-lean syngas 119 is combined with a second portion of raw syngas 120 to form the H2-adjusted syngas 116 of a lower H2/CO or (H2−CO2)/(CO+CO2) ratio than the raw syngas 106. The flow rates of the second portion of raw syngas 120 and the H2-lean stream 118 are controlled to create the H2/CO ratio effective for the hydrocarbon synthesis unit 108 to produce the desired synthetic hydrocarbon product 122. For example, a F-T process operates efficiently with an H2/CO ratio of between about 1.8 to about 2.1. A preferred F-T process operates with an H2/CO ratio of about 1.9.

In another embodiment (not shown in FIG. 1), the process produces an H2-adjusted syngas 116 by combining the H2-rich syngas 124 exiting the membrane separator 112 to form the H2-adjusted syngas 116 with an H2/CO ratio that was greater than the raw syngas 106. Thus, a synthetic hydrocarbon process requiring a H2/CO ratio that is higher than the raw syngas 106 may be fed from the syngas production hub 104. A preferred synthetic hydrocarbon unit that requires a relatively high H2/CO2 ratio is an MeOH unit. A preferred MeOH process will require a feed with an (H2−CO2)/(CO+CO2) ratio of greater than about 1.8, preferably above about 1.9, and more preferably about 2.0.

Still referring to FIG. 1, a second H2-adjusted syngas 126 is fed to a second hydrocarbon synthesis unit 110 after adjustment of the H2/CO ratio in a second membrane separator 114. In this embodiment, the second H2-adjusted syngas 126 is the H2-lean syngas leaving the second membrane separator 114 without having to mix the stream with any other stream. In other alternate embodiments (not shown) the second H2-adjusted syngas 126 may be the H2-rich syngas 128 leaving the second membrane separator 114.

Any number of synthetic process units may be connected to the syngas production hub 104, and any number for H2-adjusted syngas streams may be formed using any number or combination of membrane separators and membrane separator outlet streams. The properly composed feed gas is then fed to the respective hydrocarbon synthetic units to form the desired synthetic hydrocarbon product. Furthermore, alternate embodiments may include PSA units wherein the H2-rich gases from the membrane separators are routed to produce substantially pure H2.

Figure 2:
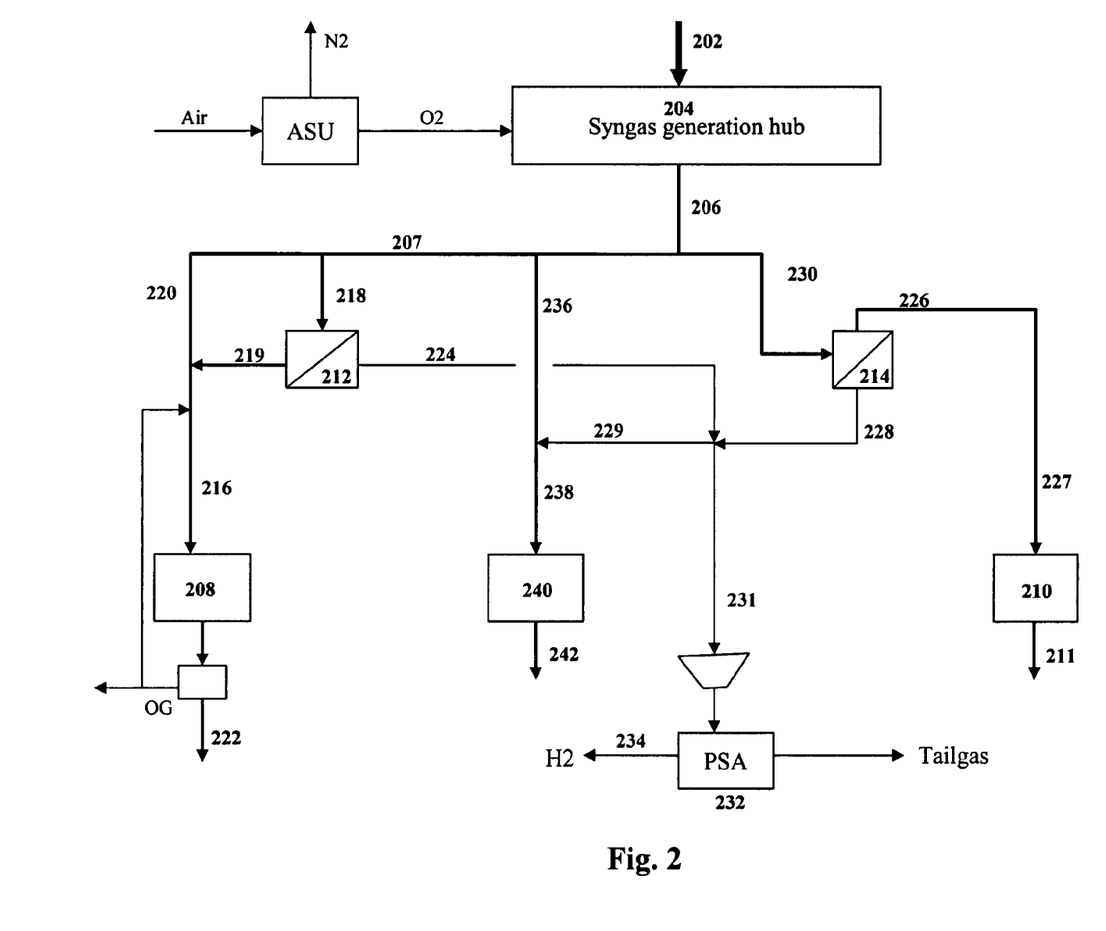
FIG. 2 is a schematic diagram of a second embodiment of the current invention.

In the embodiment of FIG. 2, a number of membrane separators 212, 214 are used to adjust the H2/CO or (H2−CO2)/(CO+CO2) ratio of the raw syngas 206 before being fed to the hydrocarbon synthesis units 208, 210, 240. The membrane separators may contain any membranes known to one of ordinary skill in the art that can affect the H2/CO ratio or (H2−CO2)/(CO+CO2) ratio of a feed gas. A preferred membrane would be a hydrogen-selective membrane, wherein hydrogen is the predominant permeate fluid. The process forms at least one H2-adjusted syngas 216 of different H2/CO or (H2−CO2)/(CO+CO2) ratio effective for the production of a desired synthetic hydrocarbon product. The H2-adjusted syngas 216 of this embodiment has, but is not limited to, an H2/CO ratio that is lower than the raw syngas 206.

Referring to one preferred embodiment exemplified in FIG. 2, an H2-adjusted syngas 216 is produced by feeding a first portion of raw syngas 218 to a first membrane separator 212 to produce a first H2-lean syngas 219 and a first H2-rich syngas 224. The first H2-lean syngas 219 is combined with a second portion of raw syngas 220 to form the first H2-adjusted syngas 216 of a lower H2/CO or (H2−CO2)/(CO+CO2) ratio than the raw syngas 206. The flow rates of the second portion of raw syngas 220 and the first H2-lean syngas 219 are controlled to create the composition effective for a first hydrocarbon synthesis unit 208 to produce a first synthetic hydrocarbon product 222. In one preferred embodiment, the first H2-adjusted syngas has an H2/CO ratio of below about 2.1. An F-T process is one preferred process for the first hydrocarbon synthesis unit 208.

Still referring to FIG. 2, a third portion of raw syngas 230 is fed to a second membrane separator 214 to form a second H2-lean syngas 226 and a second H2-rich syngas 228. The second H2-lean syngas 226 is then fed to a second hydrocarbon synthesis unit 210 as a second H2-adjusted syngas 227. In this preferred embodiment, the second hydrocarbon synthesis unit 210 requires a lower H2/CO ratio that the raw syngas 206. Still further, one preferred second hydrocarbon synthesis unit is a DME production process known to one of ordinary skill in the art. In one preferred embodiment, the second H2-adjusted syngas has an H2/CO ratio of less than about 1.8.

Still referring to FIG. 2, a portion or all of the first H2-rich syngas 224, the second H2-rich syngas 228, or a combination thereof may be combined with a fourth portion of raw syngas 236 to form a third H2-adjusted syngas 238. The third H2-adjusted syngas 238 is then fed to a third hydrocarbon synthesis unit 240 to form a third synthetic hydrocarbon product 242. The flowrates of the first H2-rich syngas 224, the second H2-rich syngas 228, or a combination of the first H2-rich syngas 224 and the second H2-rich syngas 228, and the fourth portion of raw syngas 236 are controlled to create the composition effective for the third hydrocarbon synthesis unit 240 to produce the desired third synthetic hydrocarbon product 242. In one preferred embodiment, the third H2-adjusted syngas has a (H2−CO2)/(CO+CO2) ratio of above about 1.8. The MeOH process is one preferred process for the third hydrocarbon synthesis unit 240.

Alternately, the first H2-rich syngas 224, second H2-rich syngas 228, or combination of the two streams may be fed to a PSA unit 232 to produce a substantially pure H2 234. This alternative may be practiced in addition to or instead of using the first H2-rich syngas 224, the second H2-rich syngas 228, or combination thereof to form the third H2-adjusted syngas 238. Furthermore, the first H2-rich syngas 224 and/or second H2-rich syngas 228 may be fed to any other processes as required to adjust the composition of streams in those processes.

Again referring to FIG. 2, alternate embodiments (not shown) may include combining the first H2-rich syngas 224, second H2-rich syngas 228, or combination thereof with the fourth portion of raw syngas 236 to form the third H2-adjusted syngas 238 of a composition effective to form the third synthetic hydrocarbon product 242.

Figure 3:
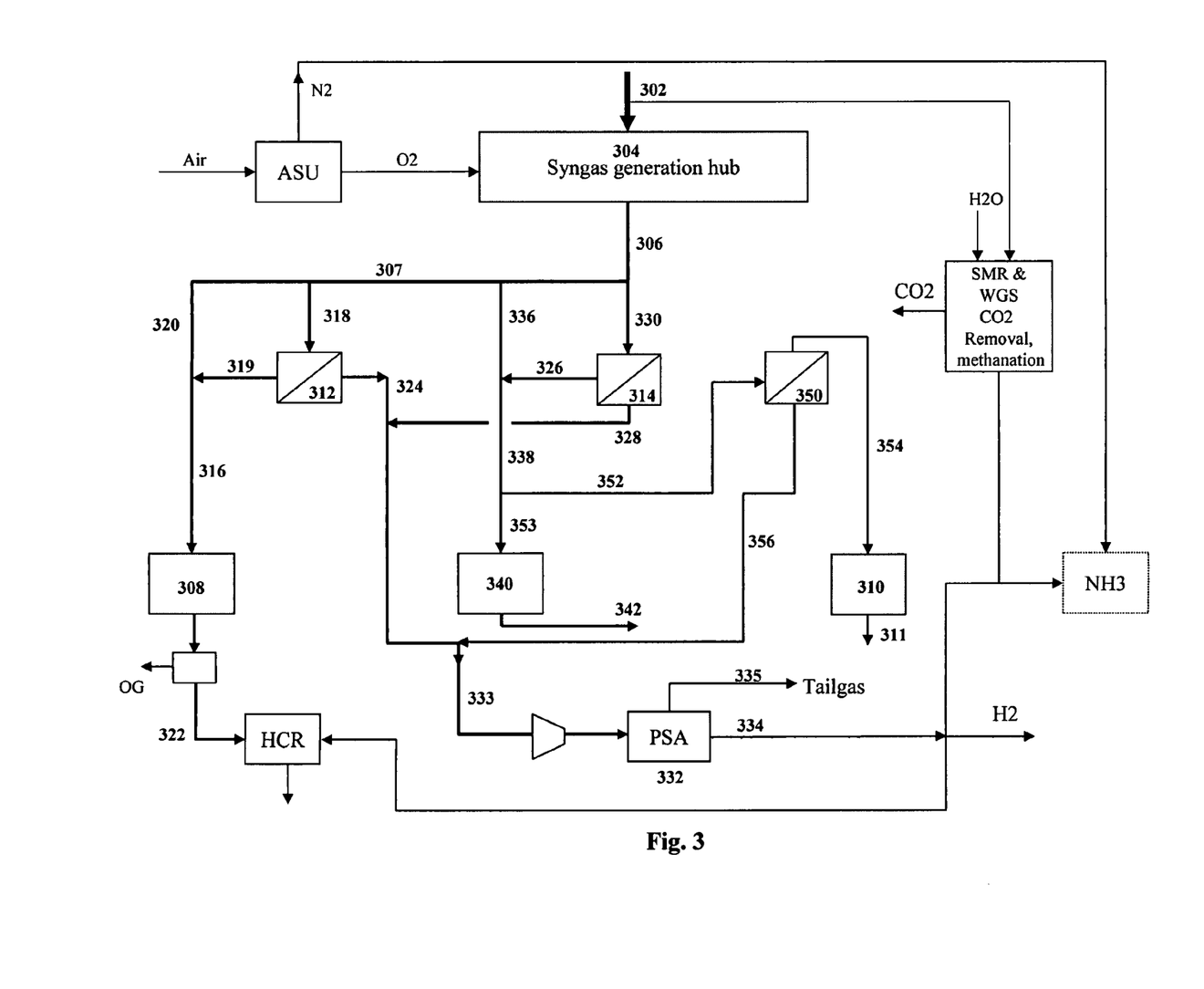
FIG. 3 is a schematic diagram of a third embodiment of the current invention.

Referring to FIG. 3, one preferred embodiment includes an integrated hydrocarbon processing system that comprises a first synthesis unit 308, a second synthesis unit 340, a first membrane separator 312, and a second membrane separator 314. A first H2-adjusted syngas 316 is produced by feeding a first portion of raw syngas 318 to a first membrane separator 312 to produce a first H2-lean syngas 319 and a first H2-rich syngas 324. The first H2-lean syngas 319 is combined with a second portion of raw syngas 320 to form the first H2-adjusted syngas 316 of a lower H2/CO or (H2−CO2)/(CO+CO2) ratio than the raw syngas 306. The flow rates of the second portion of raw syngas 320 and the first H2-lean syngas 319 are controlled to create the H2/CO ratio effective for a first hydrocarbon synthesis unit 308 to produce a first synthetic hydrocarbon product 322. In one preferred embodiment, the first H2-adjusted syngas has an H2/CO ratio of below about 2.1. An F-T process is one preferred process for the first hydrocarbon synthesis unit 308.

Still referring to FIG. 3, a third portion of said raw syngas 330 is fed to the second membrane separator 314 to form a second H2-lean syngas 326 and a second H2-rich syngas 328. The first H2-lean syngas 319, second H2-lean syngas 326, or a combination of the two streams is combined with a fourth portion of raw syngas 336 to form a second H2-adjusted syngas 338 of a composition effective for forming a second synthetic hydrocarbon product. For example, a syngas with a composition that has a lower H2/CO or (H2−CO2)/(CO+CO2) ratio than the raw syngas 306 may be required to form the second synthetic hydrocarbon product. The flow rates of the fourth portion of raw syngas 336 and the first H2-lean syngas 319, second H2-lean syngas 326, or combination thereof are controlled to create the composition effective for a second hydrocarbon synthesis unit 340 to produce a second synthetic hydrocarbon product 342. In one preferred embodiment, the second H2-adjusted syngas 338 has an (H2−CO2)/(CO+CO2) ratio of above about 1.8. In another preferred embodiment, the second H2-adjusted syngas 338 has an (H2−CO2)/(CO+CO2) ratio of above about 2.0. The MeOH process is one preferred process for the second hydrocarbon synthesis unit 340.

Referring again to FIG. 3, in one alternate embodiment, the integrated hydrocarbon processing system further comprises a third synthesis unit 310 and a third membrane separator 350. In this embodiment, a first portion of the second H2-adjusted syngas 352 is fed to the third membrane separator 350 where a third H2-lean syngas 354 and a third H2-rich syngas 356 are produced. A second portion of the second H2-adjusted syngas 353 is fed to the second synthesis unit 340 to produce a second synthetic hydrocarbon product 342. The third H2-lean syngas 354 is fed to the third synthesis unit 310 to produce a third synthetic hydrocarbon product 311. In one preferred embodiment, the H2/CO ratio of the third H2-lean syngas 354 is less than about 1.8 and more preferably about 1.0. In one preferred embodiment, the third synthesis unit 310 is a DME synthesis unit.

Still referring to FIG. 3, in one alternate embodiment, the integrated hydrocarbon processing system further comprises a PSA unit 332. In this embodiment, the first H2-rich syngas 324, second H2-rich syngas 328, third H2-rich syngas 356, or any combination of them may be fed to form a PSA feed gas 333. This PSA feed gas 333 is fed to the PSA unit 332 to make a substantially pure H2 stream 334 that can feed a variety of processes, including refinery hydrocrackers, ammonia units, or other hydrogen using processes.

EXAMPLES

Table 1 shows the mass balance for a process wherein the syngas hub produces a raw syngas with an H2/CO ratio of about 2.1 and a high CO2 content. In this embodiment, the integrated hydrocarbon processing system is that exemplified in FIG. 2 using three hydrocarbon synthesis units. The hydrocarbon synthesis units for this mass balance are producing F-T liquids, MeOH, and DME.

TABLE 1

| | Stream ID | | | | | | | |
|---|---|---|---|---|---|---|---|---|
| | 206 | 207 | 236 | 230 | 218 | 220 | 219 | 223 |
| CH4 | 0.015 | 0.015 | 0.015 | 0.015 | 0.015 | 0.015 | 0.025 | 0.000 |
| C2H6 | 0.000 | 0.000 | 0.000 | 0.000 | 0.000 | 0.000 | 0.000 | 0.000 |
| N2 | 0.014 | 0.014 | 0.014 | 0.014 | 0.014 | 0.014 | 0.023 | 0.311 |
| CO2 | 0.034 | 0.034 | 0.034 | 0.034 | 0.034 | 0.034 | 0.037 | 0.000 |
| CO | 0.299 | 0.299 | 0.299 | 0.299 | 0.299 | 0.299 | 0.479 | 0.272 |
| H2O | 0.000 | 0.000 | 0.000 | 0.000 | 0.000 | 0.000 | 0.000 | 0.000 |
| H2 | 0.637 | 0.637 | 0.637 | 0.637 | 0.637 | 0.637 | 0.435 | 0.397 |
| Ar | 0.001 | 0.001 | 0.001 | 0.001 | 0.001 | 0.001 | 0.002 | 0.020 |
| NM3/h | 820,055 | 332,614 | 438,697 | 48,744 | 66,523 | 266,091 | 38,996 | 32,590 |
| P (psia) | 360 | 360 | 360 | 360 | 360 | 360 | 350 | 350 |
| T © | 40 | 70 | 70 | 70 | 70 | 70 | 70 | 70 |
| H2/CO | 2.1 | 2.1 | 2.1 | 2.1 | 2.1 | 2.1 | — | 1.5 |
| (H2 − CO2)/(CO + CO2) | 1.81 | 1.81 | 1.81 | 1.81 | 1.81 | 1.81 | 0.77 | 1.46 |

| | Stream ID | | | | | | |
|---|---|---|---|---|---|---|---|
| | 216 | 224 | 228 | 229 | 238 | 227 | 231 |
| CH4 | 0.015 | 0.001 | 0.001 | 0.001 | 0.014 | 0.024 | 0.001 |
| C2H6 | 0.000 | 0.000 | 0.000 | 0.000 | 0.000 | 0.000 | 0.000 |
| N2 | 0.044 | 0.001 | 0.001 | 0.001 | 0.013 | 0.022 | 0.001 |
| CO2 | 0.031 | 0.029 | 0.029 | 0.029 | 0.034 | 0.037 | 0.029 |
| CO | 0.317 | 0.044 | 0.041 | 0.043 | 0.274 | 0.458 | 0.043 |
| H2O | 0.000 | 0.000 | 0.000 | 0.000 | 0.000 | 0.000 | 0.000 |
| H2 | 0.591 | 0.924 | 0.927 | 0.925 | 0.665 | 0.458 | 0.925 |
| Ar | 0.003 | 0.000 | 0.000 | 0.000 | 0.001 | 0.001 | 0.000 |
| NM3/h | 337,678 | 27,526 | 18,630 | 46,156 | 484,619 | 30,114 | 234 |
| P (psia) | 350 | 100 | 100 | 100 | 356 | 360 | 100 |
| T © | 70 | 70 | 70 | 70 | 70 | 70 | 70 |
| H2/CO | 1.9 | 21.1 | 22.4 | 21.6 | 2.4 | 1.0 | 21.6 |
| (H2 − CO2)/(CO + CO2) | 1.61 | 12.22 | 12.83 | 12.46 | 2.05 | 0.85 | 12.46 |

Table 2 shows the mass balance for a process wherein the syngas hub produces a raw syngas with an H2/CO ratio of about 2.3 and a low CO2 content. In this embodiment, the integrated hydrocarbon processing system is that exemplified in FIG. 3 using three hydrocarbon synthesis units. The hydrocarbon synthesis units for this mass balance are producing F-T liquids, MeOH, and DME.

TABLE 2

| | Stream ID | | | | | | |
|---|---|---|---|---|---|---|---|
| | 306 | 307 | 320 | 318 | 319 | 324 | 316 |
| CH4 | 0.015 | 0.015 | 0.015 | 0.015 | 0.026 | 0.001 | 0.017 |
| C2H6 | 0.000 | 0.000 | 0.000 | 0.000 | 0.000 | 0.000 | 0.000 |
| N2 | 0.015 | 0.015 | 0.015 | 0.015 | 0.026 | 0.001 | 0.017 |
| CO2 | 0.006 | 0.006 | 0.006 | 0.006 | 0.007 | 0.005 | 0.006 |

TABLE 2-continued

| | | | | | | | |
|---|---|---|---|---|---|---|---|
| CO | 0.292 | 0.292 | 0.292 | 0.292 | 0.493 | 0.042 | 0.331 |
| H2O | 0.000 | 0.000 | 0.000 | 0.000 | 0.000 | 0.000 | 0.000 |
| H2 | 0.672 | 0.672 | 0.672 | 0.672 | 0.449 | 0.951 | 0.629 |
| NM3/h | 1,000,000 | 500,000 | 350,000 | 150,000 | 83,396 | 66,604 | 433,396 |
| P (psia) | 365 | 360 | 360 | 360 | 356 | 100 | 356 |
| T © | 40 | 70 | 70 | 70 | 70 | 70 | 70 |
| H2/CO | 2.30 | 2.30 | 2.30 | 2.30 | 0.91 | — | 1.90 |
| (H2 − CO2)/(CO + CO2) | 2.23 | 2.23 | 2.23 | 2.23 | 0.89 | 20.15 | 1.85 |

| | Stream ID | | | | | | |
|---|---|---|---|---|---|---|---|
| | 336 | 330 | 326 | 328 | 338 | 353 | 352 |
| CH4 | 0.015 | 0.015 | 0.019 | 0.001 | 0.016 | 0.016 | 0.016 |
| C2H6 | 0.000 | 0.000 | 0.000 | 0.000 | 0.000 | 0.000 | 0.000 |
| N2 | 0.015 | 0.015 | 0.019 | 0.001 | 0.016 | 0.016 | 0.016 |
| CO2 | 0.006 | 0.006 | 0.006 | 0.005 | 0.006 | 0.006 | 0.006 |
| CO | 0.292 | 0.292 | 0.360 | 0.043 | 0.309 | 0.309 | 0.309 |
| H2O | 0.000 | 0.000 | 0.000 | 0.000 | 0.000 | 0.000 | 0.000 |
| H2 | 0.672 | 0.672 | 0.597 | 0.949 | 0.653 | 0.653 | 0.653 |
| NM3/h | 350,000 | 150,000 | 118,097 | 31,903 | 468,097 | 280,858 | 187,239 |
| P (psia) | 360 | 360 | 356 | 150 | 356 | 356 | 356 |
| T © | 70 | 70 | 70 | 70 | 70 | 70 | 70 |
| H2/CO | 2.30 | 2.30 | 1.66 | — | — | 2.11 | 2.11 |
| (H2 − CO2)/(CO + CO2) | 2.23 | 2.23 | 1.61 | 19.45 | 2.05 | 2.05 | 2.05 |

| | Stream ID | | | | |
|---|---|---|---|---|---|
| | 354 | 356 | 333 | 334 | 335 |
| CH4 | 0.025 | 0.001 | 0.001 | 0.000 | 0.007 |
| C2H6 | 0.000 | 0.000 | 0.000 | 0.000 | 0.000 |
| N2 | 0.025 | 0.002 | 0.001 | 0.000 | 0.008 |
| CO2 | 0.007 | 0.005 | 0.005 | 0.000 | 0.030 |
| CO | 0.472 | 0.046 | 0.044 | 0.001 | 0.249 |
| H2O | 0.000 | 0.000 | 0.000 | 0.000 | 0.000 |
| H2 | 0.472 | 0.946 | 0.948 | 0.999 | 0.707 |
| NM3/h | 115,847 | 71,391 | 169,898 | 140,260 | 29,639 |
| P (psia) | 350 | 100 | 100 | 300 | 20 |
| T © | 70 | 70 | 70 | 40 | 40 |
| H2/CO | 1.00 | | | | |

Although the present invention has been described in considerable detail with reference to certain preferred versions thereof, other versions are possible. For example, where process streams are combined, the combination can occur as indicated in the described embodiments, or can be of other combinations of streams as required to obtain the desired composition. Furthermore, separation membrane devices, hydrocarbon synthesis units and other units described herein may vary in construction. For example, one hydrocarbon synthesis unit may use equipment referred to as hydrocracker, whereas another may use a catalyst process. Furthermore, there are also a variety of devices known in the art to construct and control the described devices. Therefore, the spirit and scope of the appended claims should not be limited to the description of the preferred versions contained herein.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A process for converting syngas into at least first and second products, the first product comprising a first liquid hydrocarbon and the second product comprises a member selected from the group consisting of a second liquid hydrocarbon, methanol and dimethyl ether, the first and second liquid hydrocarbons being non-identical, the process comprising the steps of:
   (a) supplying a raw syngas comprising $H_2$;
   (b) providing an integrated hydrocarbon synthesis system comprising:
      (1) first and second synthesis units; and
      (2) first and second membrane separators;
   (c) feeding a first portion of said raw syngas to said first membrane separator;
   (d) separating said first portion of raw syngas in said first membrane separator into a first H2-lean syngas and a first H2-rich syngas;
   (e) forming a first H2-adjusted syngas by combining a second portion of said raw syngas and a stream of said first H2-lean syngas;

(f) feeding said first H2-adjusted syngas to said first synthesis unit and synthesizing thereat said first product comprising a first hydrocarbon;

(h) feeding a third portion of said raw syngas to said second membrane separator;

(i) separating said third portion of raw syngas in said second membrane separator into a second H2-lean syngas and a second H2-rich syngas; and (i) feeding a second H2-adjusted syngas to said second synthesis unit and synthesizing thereat said second product, wherein:

(1) when said second product comprises said second liquid hydrocarbon, said second H2-adjusted syngas comprises said second H2-lean syngas from said second membrane separator;

(2) when said second product comprises said dimethyl ether, said second H2-adjusted syngas comprises said second H2-lean syngas from said second membrane separator;

(3) when said second product comprises said methanol, said second H2-adjusted syngas comprises a member selected from the group consisting of said first H2-rich syngas and said second H2-rich syngas.

2. The process of claim 1, wherein said second product is said second liquid hydrocarbon.

3. The process of claim 1, wherein said second product is said dimethyl ether.

4. The process of claim 1, wherein said second product is either said second liquid hydrocarbon or said dimethyl ether and said integrated hydrocarbon synthesis system further comprises a methanol synthesis unit, and wherein said process further comprises the steps of:

(a) forming a third H2-adjusted syngas by combining a fourth portion of said raw syngas and a stream selected from the group consisting of said first H2-rich syngas, said second H2-rich syngas, and combinations thereof; and (b) feeding said third H2-adjusted syngas to said methanol synthesis unit and producing said methanol thereat.

5. The process of claim 1, wherein said first membrane separator comprises a membrane comprising materials selected from the group consisting of polyimide polymers, ceramic materials, or combinations thereof.

6. The process of claim 1, wherein said second membrane separator comprises a membrane comprising materials selected from the group consisting of polyimide polymers, ceramic materials, or combinations thereof.

7. The process of claim 1, wherein said integrated hydrocarbon synthesis system further comprises a PSA unit, and wherein said process further comprises the steps of:

(a) feeding a stream selected from the group consisting of at least a portion of said first H2-rich syngas, at least a portion of said second H2-rich syngas, and combinations thereof to a PSA unit; and (b) obtaining a substantially pure H2 stream.

8. The process of claim 1, wherein said integrated hydrocarbon synthesis system further comprises an autothermal reforming unit wherein a natural gas feed reacts with an oxygen stream to form said raw syngas.

9. The process of claim 1, wherein said integrated hydrocarbon synthesis system further comprises a PSA unit, and wherein said process further comprises the steps of:

(a) combining at least two members selected from the group consisting of said first H2-rich syngas, said second H2-rich syngas, and said third H2-rich syngas to form a PSA feed gas;

(b) feeding said PSA feed gas to a PSA unit and obtaining a substantially pure H2 stream thereat.

10. The process of claim 1 wherein said second product is said methanol.

* * * * *